United States Patent
Gaisnon et al.

(10) Patent No.: US 8,499,622 B2
(45) Date of Patent: Aug. 6, 2013

(54) DEVICE FOR CHECKING A TURBOMACHINE ENGINE

(75) Inventors: Patrick Gaisnon, Moissy Cramayel Cedex (FR); Quentin Mistral, Moissy Cramayel Cedex (FR); Sylvie Mozer, Moissy Cramayel Cedex (FR); Nicolas Samak, Moissy Cramayel Cedex (FR)

(73) Assignee: SNECMA, Paris (FR)

( * ) Notice: Subject to any disclaimer, the term of this patent is extended or adjusted under 35 U.S.C. 154(b) by 0 days.

(21) Appl. No.: 13/377,429

(22) PCT Filed: Jul. 1, 2010

(86) PCT No.: PCT/FR2010/051383
§ 371 (c)(1),
(2), (4) Date: Dec. 9, 2011

(87) PCT Pub. No.: WO2011/004101
PCT Pub. Date: Jan. 13, 2011

(65) Prior Publication Data
US 2012/0085156 A1 Apr. 12, 2012

(30) Foreign Application Priority Data

Jul. 9, 2009 (FR) .................................... 09 03400

(51) Int. Cl.
*G01M 15/14* (2006.01)
(52) U.S. Cl.
USPC ..................................................... 73/112.01
(58) Field of Classification Search
USPC ..................................................... 73/112.01
See application file for complete search history.

(56) References Cited

U.S. PATENT DOCUMENTS

| | | | |
|---|---|---|---|
| 4,139,822 A * | 2/1979 | Urich et al. | 324/219 |
| 4,149,419 A | 4/1979 | Connell, Jr. et al. | |
| 6,036,636 A * | 3/2000 | Motoki et al. | 600/146 |
| 6,867,586 B2 * | 3/2005 | Hatcher et al. | 324/239 |
| 6,943,570 B2 * | 9/2005 | Duffy et al. | 324/718 |
| 7,768,259 B2 * | 8/2010 | Cabanis et al. | 324/220 |
| 8,299,785 B2 * | 10/2012 | Bousquet et al. | 324/220 |
| 2007/0055103 A1 | 3/2007 | Hoefig et al. | |
| 2009/0079821 A1 * | 3/2009 | Bousquet et al. | 348/65 |
| 2011/0018530 A1 | 1/2011 | Bousquet et al. | |
| 2011/0178727 A1 * | 7/2011 | Hafenrichter et al. | 702/38 |
| 2012/0291583 A1 * | 11/2012 | Bousquet et al. | 74/490.04 |

FOREIGN PATENT DOCUMENTS

| | | |
|---|---|---|
| EP | 1 759 629 | 3/2007 |
| WO | 98 32380 | 7/1998 |

OTHER PUBLICATIONS

International Search Report Issued Nov. 11, 2010 in PCT/FR10/51383 Filed Jul. 1, 2010.

* cited by examiner

*Primary Examiner* — Freddie Kirkland, III
(74) *Attorney, Agent, or Firm* — Oblon, Spivak, McClelland, Maier & Neustadt, L.L.P.

(57) ABSTRACT

A device for non-destructive in situ inspection of parts of a turbine engine, the device including a stick carrying at its distal end a pivoting finger carrying at one of its ends a blade for supporting an inspection probe, and at its opposite end a skid for bearing against and/or catching on an element of the engine, the skid being movable in a direction parallel to the longitudinal axis of the finger.

11 Claims, 2 Drawing Sheets

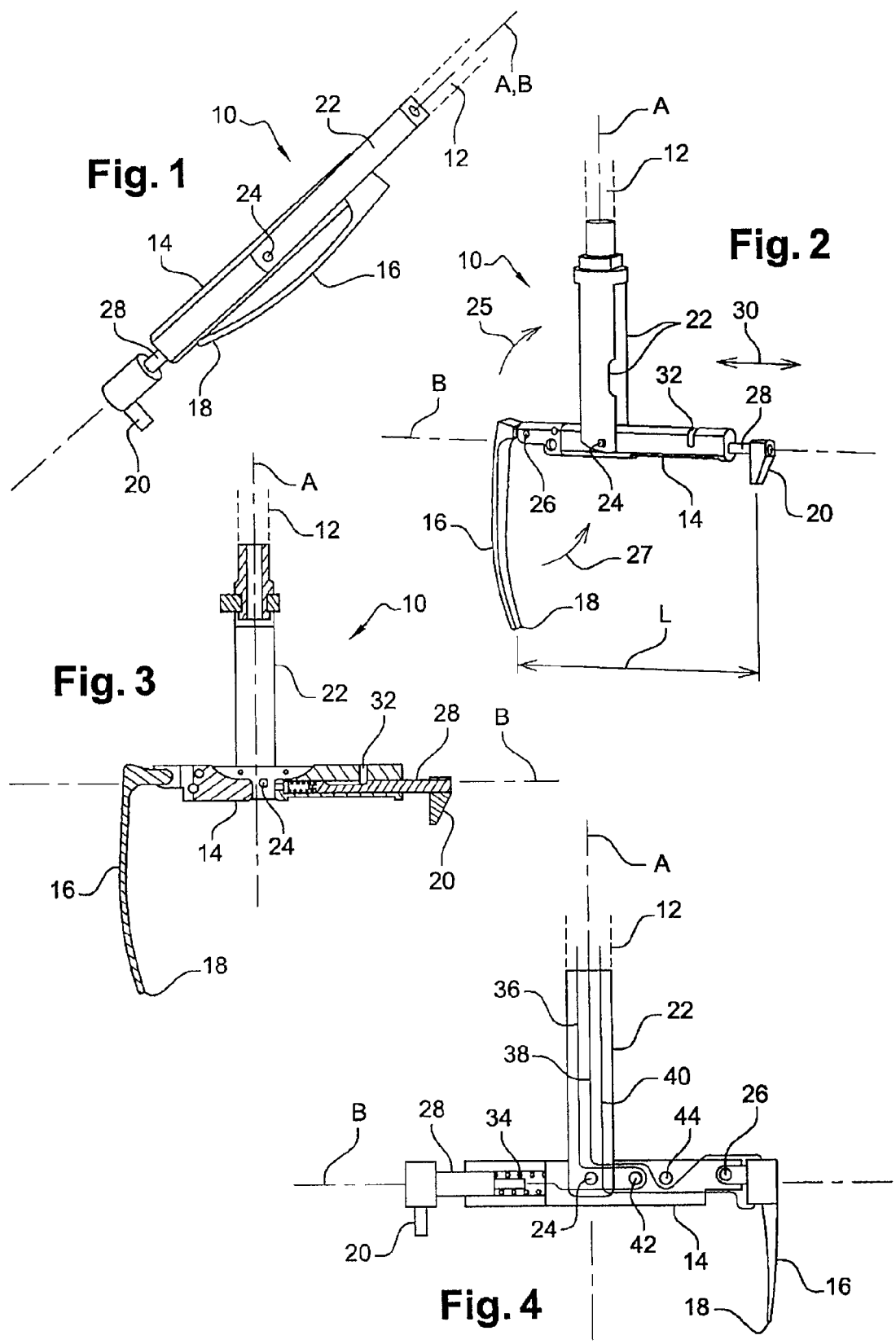

DEVICE FOR CHECKING A TURBOMACHINE ENGINE

BACKGROUND OF THE INVENTION

1. Field Of The Invention

The present invention relates to a device for non-destructive in situ inspection of parts of an engine, in particular a turbine engine.

2. Description Of The Related Art

Non-destructive inspection (NDI) of parts of a turbine engine serve to verify the state of such parts without damaging them. Under certain circumstances, such inspection may require the engine to be removed and partially dismantled in order to inspect parts that are difficult to access with inspection means.

A known inspection device comprises a rigid stick carrying an inspection probe or a sensor at its distal end. When the turbine engine is fitted with endoscopic orifices, the stick is inserted into the turbine engine through one of these orifices in order to perform in situ inspection of parts of the turbine engine, thereby avoiding any need to remove the engine or to dismantle it.

Nevertheless, the zone that is accessible to the stick is very limited and generally lies in register with the endoscopic orifice and at a short distance therefrom. Furthermore, when the probe carried by the stick needs to be used on a part, the probe needs to be pressed against a surface of said part with a certain amount of pressure and for a determined duration, and that is not always possible with the above-mentioned device.

For example, with labyrinth seals in a turbine engine, the outer annular wipers carried by the rotor of the turbine engine co-operate with blocks of abradable material carried by inner annular platforms of stator vanes of the turbine engine. In order to access the wipers of a labyrinth seal, it is therefore necessary to pass the inspection probe into a very narrow space that may present a width or axial dimension of about 1 millimeter (mm), and that is not possible with the above-mentioned stick.

As a result, certain zones of a turbine engine remain difficult to access for known non-destructive inspection devices since they are not designed to pass through orifices or passages of small size and through a plurality of consecutive orifices and/or passages that are not in alignment.

Furthermore, while inspecting a part, the probe generally needs to be held stationary relative to the engine, which is difficult with the above-mentioned prior art stick.

BRIEF SUMMARY OF THE INVENTION

The invention proposes a solution to the problems of the prior art that is simple, effective, and inexpensive.

A particular object of the invention is to provide a non-destructive inspection device making it possible to inspect parts regardless of their positions and their accessibility within a turbine engine, and to hold the inspection sensor or probe stationary while performing an inspection step.

To this end, the invention provides a device for non-destructive in situ inspection of parts of an engine, in particular a turbine engine, the device comprising a longitudinal stick having an inspection probe mounted at the distal end thereof, the device being characterized in that it comprises a longitudinal finger pivotally mounted to the distal end of the stick, the finger carrying at a first end support means for supporting the inspection probe, and at a second end catch means for catching on an element of the engine, these catch means being movable in a direction parallel to the finger.

The movement of the catch means of the device of the invention in a direction parallel to the finger enables them to be moved away from or towards the inspection probe support means as a function of the specific surroundings of the engine parts for inspection. The catch means are designed to bear against an element of the engine so as to stabilize the device while it is inspecting parts. By way of example, an element of the engine may be clamped between the support means and the catch means of the device of the invention in order to hold the device stationary while performing an inspection operation. The support means of the probe are designed to be inserted in spaces that are very narrow so as to position the inspection probe in locations of the engine that are difficult to access.

According to another characteristic of the invention, the support means comprise a blade of elongate shape that is pivotally mounted via one of its ends to the first end of the finger to pivot between a folded position in which it extends substantially parallel to the finger and a deployed position in which it extends substantially perpendicularly to the finger.

At rest, the support blade supporting the inspection probe is preferably elongate in shape and slightly curved about its long axis. The blade of the invention is advantageously elastically deformable in bending, thereby making it possible in particular to press the probe with a certain amount of pressure (corresponding to bending the blade) against the surface of the part for inspection, whenever said probe needs to press against the part it is inspecting. The blade is also movable in pivoting between a folded position in which it extends along and beside the finger, and a deployed position in which it extends substantially perpendicularly to the finger. The blade is brought into the folded position before the stick is inserted into the turbine engine so as to protect the probe against possible impacts against surrounding parts. The blade may be pivoted by means of a cable, e.g. of the "piano-wire" type, that extends along the stick and that is connected at its distal end to the blade. The device may include resilient return means urging the blade into its folded position or its deployed position.

The inspection probe may be fastened to a free end of the blade, e.g. by adhesive. By way of example, the inspection probe may be an eddy current sensor or an ultrasound sensor or a mini-camera.

Advantageously, the finger is pivotally mounted in its middle portion to the distal end of the stick, to pivot between a folded position in which it extends substantially parallel to the stick and a deployed position in which it extends substantially perpendicularly to the stick. This makes it possible further to increase the zones that can be accessed by the device of the invention. Pivoting of the finger may be controlled by a cable, e.g. of the "piano-wire" type, that extends along the stick and that is connected at its distal end to the finger or to the blade.

The above-mentioned cables may be housed inside the stick and may be connected to appropriate control means situated at the proximal end of the stick.

The device may also include resilient return means urging the finger into its folded position or its deployed position.

The catch means of the device of the invention may comprise a rod slidably mounted in a corresponding axial recess at the second end of the finger and it may carry a bearing tab at its free end that extends substantially perpendicularly to the rod.

The movement of the catch means may be controlled by at least one cable extending along the stick and connected at its distal end to the end of the rod that is opposite from the bearing tab.

BRIEF DESCRIPTION OF THE SEVERAL VIEWS OF THE DRAWINGS

The invention can be better understood and other details, characteristics, and advantages of the present invention appear more clearly on reading the following description made by way of non-limiting example and with reference to the accompanying drawings, in which:

FIG. 1 is a fragmentary diagrammatic view of an inspection device of the invention, shown in its folded or stowed position;

FIG. 2 is a fragmentary diagrammatic view in perspective of the FIG. 1 device, shown in its deployed position;

FIG. 3 is a diagrammatic axial section view of the FIG. 1 device, in its deployed position;

FIG. 4 is another highly diagrammatic view in axial section of the FIG. 1 device, and it shows the control means of the device.

DETAILED DESCRIPTION OF THE INVENTION

Figure 5:
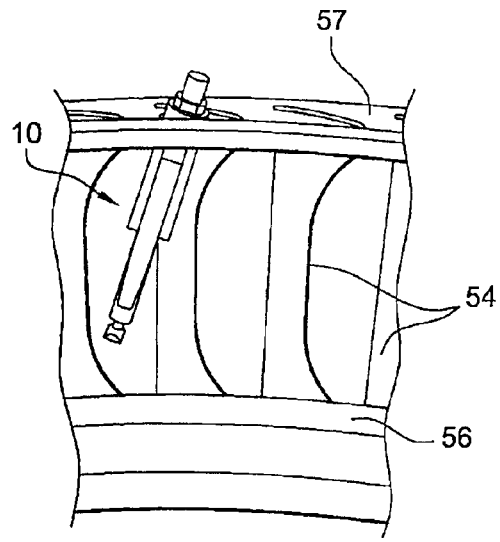
FIGS. 5 to 8 are diagrammatic perspective views of a portion of a turbine engine in which the device of FIGS. 1 to 4 is inserted for in situ inspection of parts, the figures showing different steps in the positioning of the device inside the engine.
Figure 6:
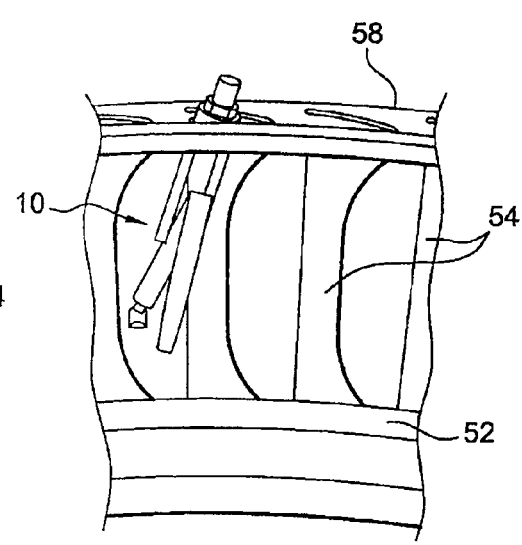
Figure 7:
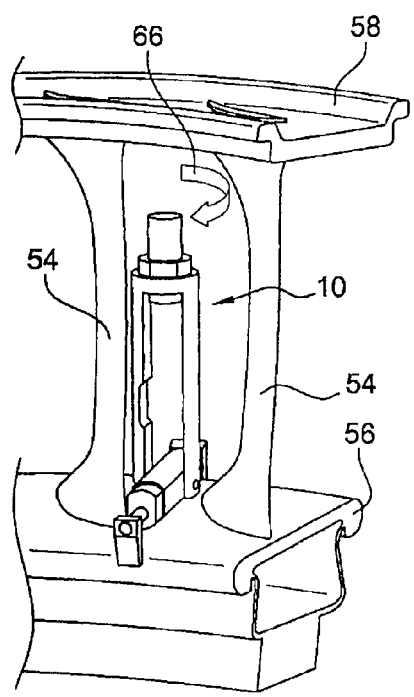

Reference is made initially to FIGS. 1 to 4 that show a device 10 of the invention for non-destructive inspection of parts of a turbine engine, the engine being described in part below with reference to FIGS. 5 to 8.

The device 10 comprises a longitudinal stick 12 (shown in dashed lines) having a finger 14 pivotally mounted at the distal end thereof, the finger carrying at one of its ends a blade 16 for supporting an inspection probe 18, and at its opposite end a skid 20 for bearing against and/or catching on an element of the engine.

The stick 12 carries at its distal end two longitudinal tabs 22 that are parallel and spaced apart, with the finger 14 being pivotally mounted via its middle portion on a pin 24 that extends between the free ends of the tabs 22.

The finger 14 is movable in pivoting (arrow 25) between a folded position as shown in FIG. 1 in which it extends between the tabs and parallel to the longitudinal axis A of the stick, and a deployed position as shown in FIGS. 2 to 4 in which it extends perpendicularly to said axis A.

The blade 16 is elongate in shape and is pivotally mounted (arrow 27) via one of its ends about a pin 26 carried by one of the ends of the finger 14, to pivot between a folded position as shown in FIG. 1 in which it extends along the finger, and a deployed position as shown in FIGS. 2 to 4 in which it extends perpendicularly to the axis B of the finger. The blade is preferably releasably fastened on the finger so as to be capable of being replaced by another blade, e.g. in the event of the blade or the probe becoming worn or in order to change the type of probe.

The blade 16 is relatively thin and is elastically deformable in bending. The inspection probe 18, e.g. an eddy current probe or an ultrasound probe, is fastened to the free end of the blade by adhesive. In a variant or in addition, a miniature camera may be fastened to the free end of the blade.

The skid 20 is fastened to one end of a rod 28 that is slidably mounted in a corresponding axial housing of the finger, the housing opening out in the end of the finger opposite from the blade 16. The skid 20 extends substantially parallel to and in the same direction as the blade 16, when the blade is in its deployed position (FIGS. 2 to 4).

The skid 20 is movable in translation in a direction parallel to the axis B of the finger 14 by the rod 28 sliding in the housing of the finger. Movement of the skid (arrow 30) serves to vary the distance L between the skid and the probe-support blade 16 (FIG. 2).

Resilient return means 34, such as a coil spring, are mounted around the rod 28 and urge the skid 20 towards its position furthest from the blade 16 (FIG. 4).

The finger 14 carries abutment 32 co-operating with the rod 28 to limit the movement stroke of the skid 20 relative to the finger.

FIG. 4 is a diagram of the control means for controlling the movement of the skid 20 and the pivoting of the finger 14 and of the blade 16. These control means comprise cables 36, 38, and 40, e.g. of the "piano-wire" type, which cables extend along the stick 12 and are connected at their proximal ends to suitable control means situated at the proximal end of the stick. By way of example, these cables are made of steel and they have a diameter of about 0.5 mm.

The distal end of the cable 36 is connected to the end of the rod 28 opposite from the skid 20 for the purpose of controlling the movement in translation of the skid along the axis B of the finger. When a traction force is applied to the cable 36, the skid moves towards the probe support blade 16.

The distal end of the cable 38 is connected to the end of the blade 16 that is remote from the probe 18 in such a manner that a traction force on this cable gives rise simultaneously to pivoting of the blade and of the finger from their folded positions to their respective deployed positions.

The distal end of the cable 40 is connected to the end of the blade that is opposite from the probe so that a traction force on this cable gives rise simultaneously to pivoting of the blade and of the finger from their deployed positions to their respective folded positions.

The finger 14 carries guide means 42 and 44 for guiding the above-mentioned cables so as to ensure that the forces applied on the parts for being moved by means of the cables are directed in given directions. In the example shown, the first guide means 42 for guiding the cable 36 for controlling movement of the skid 20 transform a traction force parallel to the axis of the stick 12 into a traction force parallel to the axis B of the finger. Second guide means 44 for guiding the cable 38 for controlling pivoting of the finger and of the blade transform a traction force parallel to the axis A of the stick into a traction force substantially parallel to the axis B of the finger.

The device 10 of the invention may also include resilient return means urging the finger and/or the blade into their respective deployed or folded positions.

Reference is made below to FIGS. 5 to 8, which show steps in a method of in situ inspection of parts of a turbine engine, using a device as described above.

Figure 8:
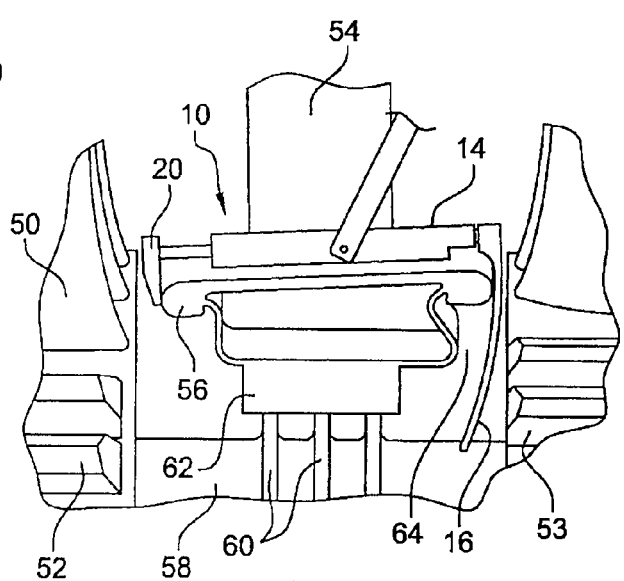

FIG. 8 is a fragmentary diagrammatic view in perspective of a turbine or compressor stage of a turbine engine. This stage comprises an annular row of rotor blades 50 carried by a disk 52, and an annular row of stator vanes 54 arranged upstream from the rotor blades 50 and extending radially between an inner annular platform 56 and an outer annular platform 57 (FIGS. 5 to 8). The inner platform 56 surrounds a rotor wall 58 that is substantially cylindrical, connecting the rotor disk 52 to another rotor disk 53 situated upstream from the stator vanes 54.

A labyrinth type seal is mounted between the rotor wall 58 and the inner platform 56 and includes annular wipers 60 extending radially outwards from the rotor wall 58 and cooperating with blocks of abradable material 62 fastened to the inner coupling of the platform 56.

The outer platform 57 includes substantially radial orifices for passing the device 10 as described above, in order to inspect parts that are difficult to access, such as the wall of the rotor 58 and the annular wipers 60.

The rotor wall 58 and the wipers 60 are inspected by means of the device 10 of the invention as follows. The finger 14 and the blade 16 are brought into their folded positions as shown in FIG. 1 with the finger 14 in alignment with the axis A of the stick 12 and the blade 16 extending along the finger. The device 10 is engaged from the outside through one of the orifices in the outer platform 57 until the finger 14 is situated between the two platforms 56 and 57 (FIG. 5), i.e. in the gas-flow passage of the compressor or the turbine. A traction force is applied to the cable 38 so that the finger 14 pivots about the pin 24 and the blade 16 pivots about the pin 26 (FIG. 6), each going from its folded position to its respective deployed position as shown in FIGS. 2 to 4. This pivoting may be made easier by the above-mentioned resilient return means of the device. The bearing skid 20 is also urged into its position furthest away from the blade 16 by the above-mentioned resilient means 34. The stick 12 is then turned about its axis A so that the free end of the blade 16 comes level with the annular space 64 that extends axially between the downstream annular edge of the inner platform 56 of the stator vanes 54 and the upstream annular edge of the disk 53. The device is moved in translation along the axis A of the stick towards the inner platform 56 until the finger 14 is situated in the vicinity of said platform and the blade 16 is engaged in the above-mentioned space 64. The finger 14 may be turned again about the axis A of the stick 12 (arrow 66 in FIG. 7) so that the skid 20 and the blade 16 come respectively to bear against the upstream and downstream annular edges of the inner platform 56. A traction force is then applied to the cable 36 so that the skid moves towards the blade and is held stationary against the upstream annular edge of the platform 56. The platform 56 is then clamped between the skid 20 and the blade 16, and the device is held stationary on the platform in order to inspect the wipers 60 (FIG. 8). In this position, the inspection probe 18 bears against the outside surface of the rotor wall 58 carrying the annular wipers 60 (FIG. 8). This causes the blade to deform elastically a little in bending such that the resilient return force holds the probe against the wall 58. It is then possible to begin inspecting the wall 58 by means of the probe 18. The rotor wall 58 is moved in rotation about its axis so as to inspect an entire annular zone (over 360°) of said wall by means of the probe.

The invention claimed is:

1. A device for non-destructive in situ inspection of parts of an engine, the device comprising:
    a longitudinal stick including an inspection probe mounted at a distal end thereof; and
    a longitudinal finger pivotally mounted to the distal end of the stick, the finger carrying at a first end support means for supporting the inspection probe, and at a second end catch means for catching on an element of the engine, the catch means being movable in a direction parallel to the finger.

2. A device according to claim 1, wherein the support means comprises a blade of elongate shape that is pivotally mounted via one of its ends to the first end of the finger to pivot between a folded position in which it extends substantially parallel to the finger and a deployed position in which it extends substantially perpendicularly to the finger.

3. A device according to claim 2, wherein the blade is elastically deformable in bending.

4. A device according to claim 2, wherein the inspection probe is fastened to the free end of the blade.

5. A device according to claim 2, further comprising resilient return means urging the blade towards its folded position or its deployed position.

6. A device according to claim 2, further comprising at least one control cable for controlling pivoting of the blade from its deployed position to its folded position and/or from its folded position to its deployed position, the control cable(s) extending along the stick.

7. A device according to claim 1, wherein the finger is pivotally mounted in its middle portion to the distal end of the stick, to pivot between a folded position in which it extends substantially parallel to the stick and a deployed position in which it extends substantially perpendicularly to the stick.

8. A device according to claim 7, further comprising resilient return means urging the finger into its folded position or its deployed position.

9. A device according to claim 7, further comprising at least one control cable for controlling pivoting of the finger from its deployed position to its folded position and/or from its folded position to its deployed position, the control cable(s) extending along the stick.

10. A device according to claim 1, wherein the catch means comprises a rod that is slidably mounted in a corresponding axial recess in the second end of the finger and that carries at its free end a bearing tab that extends substantially perpendicularly to the rod.

11. A device according to claim 10, wherein movement of the catch means is controlled by at least one cable extending along the stick and connected at its distal end to the end of the rod that is opposite from the bearing tab.

* * * * *